(12) United States Patent
Or et al.

(10) Patent No.: US 6,440,942 B1
(45) Date of Patent: Aug. 27, 2002

(54) 14-MEMBERED MACROLIDES DERIVED FROM LEUCOMYCINS

(75) Inventors: Yat Sun Or, Cambridge; Tsvetelina Lazarova, Brookline; Sophie Binet, Roslindale, all of MA (US); Jianchao Wang, Castro Valley, CA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 09/747,578

(22) Filed: Dec. 22, 2000

(51) Int. Cl.$^7$ .................. A61K 31/70; C07H 17/08
(52) U.S. Cl. .................. 514/29; 514/28; 536/7.1
(58) Field of Search .................. 536/7.1; 514/28, 514/29

(56) References Cited

U.S. PATENT DOCUMENTS

| | | | |
|---|---|---|---|
| 5,760,011 A | 6/1998 | Jaynes et al. | 514/30 |
| 6,124,269 A | 9/2000 | Phan et al. | 514/29 |

FOREIGN PATENT DOCUMENTS

| | | | |
|---|---|---|---|
| EP | 93117427.0 | 5/1994 | C07H/17/08 |
| WO | PCT/IB94/00199 | 1/1995 | C07D/407/12 |

*Primary Examiner*—Elli Peselev
(74) *Attorney, Agent, or Firm*—Gaetano D. Maccarone, Esq.

(57) ABSTRACT

There is described a novel class of ring contracted 14-membered macrolides, and pharmaceutically acceptable salts, esters and prodrugs thereof, having antibacterial activity, compositions comprising a therapeutically effective amount of a compound of the invention in combination with a pharmaceutically acceptable carrier as well as a method for treating bacterial infections by administering to a mammal a pharmaceutical composition containing a therapeutically effective amount of a compound of the invention. There are also described synthetic processes for preparing the compounds of the invention.

11 Claims, No Drawings

14-MEMBERED MACROLIDES DERIVED FROM LEUCOMYCINS

TECHNICAL FIELD

The present invention relates to novel macrolides having antibacterial activity and useful in the treatment and prevention of bacterial infections. More particularly, the invention relates to ring contracted Leucomycin analogs, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Natural macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). The most commonly used macrolides are erythromycin and josamycin.

The 16-membered ring macrolide antibiotics constitute an important clinically useful series of naturally occurring compounds within the macrolide class of antibiotics, as they show some advantages over 14-membered ring compounds (gastrointestinal tolerance and activity against strains expressing resistance of the inducible type). Sixteen membered macrolides usually contain an amino disaccharide (4-O-(L-mycarosyl)-D-mycaminose and/or D-desosamine). One class has only neutral sugars. The sixteen membered macrolides can be classified into two major groups—the leucomycins and the tylosin series.

The leucomycins, represented by Formulae Ia and Ib, are further divided, as follows, into five groups according to the chromophores:

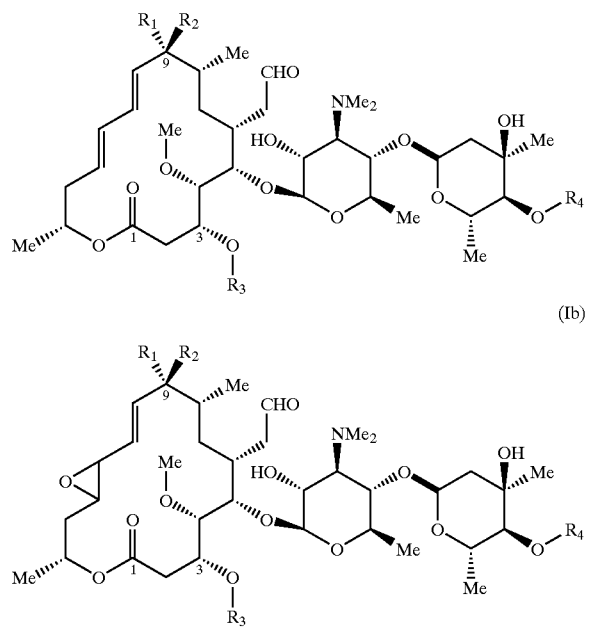

(Ia)

(Ib)

1. Leucomycin group containing platenomycin A1, A0 and C2, josamycin (leucomycin A3) and midecamycin A1 and A2.
2. Maridomycin group containing platenomycin C1.
3. Carbomycin B group containing platenomycin W1, midecamycin A4 and A3 and niddamycin
4. Carbomycin A group containing the deltamycin complex
5. Spiramycin complex.

The leucomycins, carbomycins, maridomycins, platenomycins, midecamycins and spiramycins are members of the magnamycin group of 16-membered macrolides, having D-mycaminose and L-mycarose as sugar moieties and an aglycone with an identical carbon skeleton. The antibiotics differ from each other in terms of the acyl group on positions O-3 and O-4" and the C12, 13 epoxy group. Platenolide I (or II) is the earliest lactonic intermediate in their biosynthesis.

The deoxy sugars and amino sugars in the macrolide antibiotics are biosynthesis from D-glucose with retention of carbon skeletons. The L-sugar is attached at C-3, while the D-sugar attaches at C-5.

The acyl moieties attached at positions O-3 and O-4" are derived from amino acids. Within a given chromophoric group, it is possible to differentiate the various compounds by the substituent at C-3.

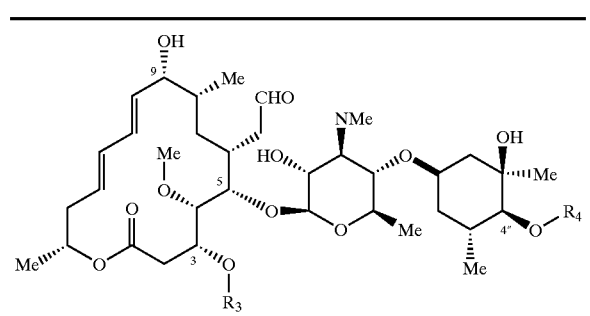

| Leucomycin | R3 | R4 |
|---|---|---|
| A1 | H | C(O)CH2CHMe2 |
| A5 | H | C(O)CH2CH2CH3 |
| A7 | H | C(O)CH2CH3 |
| A9 | H | C(O)CH3 |
| V(A11) | H | H |
| (Josamycin) A3 | C(O)CH3 | C(O)CH2CHMe2 |
| A4 | C(O)CH3 | C(O)CH2CH2CH3 |
| A6 | C(O)CH3 | C(O)CH2CH3 |
| A8 | C(O)CH3 | C(O)CH3 |
| U | C(O)CH3 | H |
| Miokamycin[1] | C(O)CH2CH3 | C(O)CH2CH2CH3 |
| Rokitamycin[2] | H | C(O)CH2CH2CH3 |

[1] 9-OAc; 3"-OAc
[2] 3"-O C(O)CH2CH3; 4"-O C(O)CH2CH2CH3

Josamycin is produced by *Streptomyces narbonensis* var. *josamyceticus*. Josamycin was found to be identical to leucomycin A3. Josamycin belongs to the leucomycin Ac group and differs from the other members by the 4"-O-substituent. Josamycin has a 4"-O-isovaleryl side-chain. In acidic aqueous solution, josamycin is transformed into isojosamycin (isoleucomycin A3) in which the hydroxyl group at C-13 is transferred from C-9. Four metabolites have been isolated from the urine and plasma of adults given oral josamycin. Two show poor antimicrobial activity [(5-hydroxyjosamycin ($O_1$) and β-hydroxyisovaleryl josamycin ($O_2$)] and two are inactive (desisovaleryl josamycin and demycarosyl josamycin or josambose). The pediatric formulation is josamycin propionate.

Leucomycin A5 is one of the components of the leucomycin complex named kitasamycin, and is produced from the fermentation broth of a strain of *Streptomyces kitasatoensis*. It was obtained as a single component by controlling the culture conditions.

Leucomycin A5 belongs to the Fr group, because it has a hydroxyl group at C-3, C-9 and C-2' and a tertiary hydroxyl group at C-3". It also has a 4"-butyryl moiety (L-mycarose) instead of a 4"-isovaleryl (A1), 4"-butyryl (A7), 4"-acetate (A9) or 4" —OH (V). Leucomycin A5 shows good antibacterial activity in vitro.

Rokitamycin is a semisynthetic 16-membered-ring macrolide obtained by attaching a propionate to the 3" position of leucomycin A5. 3"-O-propionyl leucomycin A5 is the most active derivative of 4"-O-butyryl derivatives and shows the highest serum levels in dogs and monkeys. The 3"-O-acetyl and 3"-O-butyryl derivatives were less active than 3"-O-propionyl leucomycin A5.

The in vitro activity of rokitamycin against against Gram-negative bacteria is twice as high as that of leucomycin A5, josamycin, and midecamycin. Rokitamycin is highly metabolized into four metabolites (10"-hydroxyrokitamycin, leucomycin A7, leucomycin V and 14-hydroxyleucomycin V. Leucomycin A7 and Lecomycin V (4"-debutyryl leucomycin A5) are the main metabolites). Their in vitro potency is respectively one-half and one-tenth that of the parent compound.

Midecamycins are fermentation products of *Streptomyces mycarofaciens* and include four components—A1, A2, A3, and A4. Midecamycin A1 and A2 belong to chromophoric group I, and midecamycin A3 and A4 to chromophoric group III.

Midecamycin A2, A3 and A4 are minor components of the mixture produced by *Streptomyces mycarofaciens*; the major component, A1, has been marketed.

Miokamycin is a semisynthetic 16-membered-ring macrolide derived from midecamycin A1 by introducing two acetyl groups at C-3" and C-9. A large number of acyl derivatives has been prepared by modifying the hydroxyl groups at C-9, C-2' and C-3" of midecamycin A1, in order to improve the biological activities and pharmaceutical properties.

Platenomycins were isolated from the fermentation broth of *Streptomyces platensis* MCRL 0388. Platenomycin complex is composed of nine components—$A_0$ ($YL-7_{04}$), A1 (turimycin P5), B1, C1, C2 (espinomycin A3), C4 (maridomycin II), W1, W2 and W3. The chemical structure of the different compounds has been elucidated. Platenomycin C1 was found to be identical to maridomycin III, and platenomycin B1 to midecamycin III, and platenomycin B1 to midecamycin and espinomycin A1.

Platenomycin has a 16-membered-ring lactone, one aminosugar (D-mycaminose) and one neutral sugar (L-mycarose).

The members of platenomycin complex can be differentiated by the aglycone moiety: platenolide I has a 9-hydroxyl (platenomycins W1, W2).

Carbomycin was isolated from the fermentation broth of *Streptomyces halstedii*. The carbomycin complex has two components—carbomycin A and carbomycin B.

Carbomycin A is identical to deltamycin A4. Carbomycin B (magnamycin B) is used in veterinary medicine.

Niddamycin was isolated from the fermentation broth of a strain of *Streptomyces djaktensis*. It is a substituted 16-membered lactone with an amino sugar (D-mycaminose) and a neutral sugar (L-mycarose). The D-mycaminose is bound to C-5 of the aglycone nucleus, while the L-mycarose (substituted at C-4" with an isovaleryl) binds to the C-4' hydroxyl of D-mycaminose. The lactone ring has a C-6 formylmethyl group. It has no acetyl group at C-3.

Niddamycin shows good antibacterial activity in vitro against Gram-positive bacteria and Mycoplasma spp.

Spiramycin complex consists of three major (I, II, III) and three minor components (IV, V, VI). They were derived from the fermentation broth of *Streptomyces ambofaciens*, a soil organism isolated in the north of France.

Spiramycins consist of four structural components—a 16-membered lactone (platenolide), two amino sugars (D-mycaminose and D-forosamine) and one neutral sugar (L-mycarose). Of the 16-membered-ring macrolide antibiotics, only the spiramycins bear D-forosamine. This amino-sugar is attached to position 9 of the platenolide ring. The three major components differ by the substituent at position 3, as follows: spiramycin I (3-OH), spiramycin II (3-O-acetyl) and spiramycin III (3-O-propionyl). Spiramycin IV and spiramycin VI have a secondary alcohol at C-6 instead of a formylmethyl group. Spiramycin V differs from spiramycin I by the presence of an L-mycarose instead of a D-forosamine. Spiramycin IV bears a D-forosamine and spiramycin VI an L-mycarose.

The antibacterial spectrum of the spiramycins is similar to that of other macrolide antibiotics. They are less active than erythromycin A and show antiprotozoal activity. After oral intake, a certain proportion of spiramycin is demycarsolated into neospiramycin in the stomach.

The search for macrolides active against MLS-resistant strains (MLS=Macrolides-Lincosamides-Streptogramines) has become a major goal, together with retaining the overall profile of the macrolides in terms of stability, tolerance and pharmacokinetics. Semisynthetic molecules have recently been developed from erythromycin A; new compounds containing a 14-membered lactone ring with chemical modifications to enhance acid stability and prevent anhydro formation include roxithromycin and clarithromycin.

However, less research has been done to improve the sixteen membered macrolides to overcome bacterial resistance.

SUMMARY OF THE INVENTION

The present invention provides a novel class of ring contracted 14-membered macrolides derived from the leucomycins possessing increased antibacterial activity toward Gram positive and Gram negative bacteria as well as macrolide resistant Gram positives.

In one embodiment, the present invention provides compounds represented by Formulae II or III, or a pharmaceutically acceptable salt, ester or prodrug thereof.

(II)

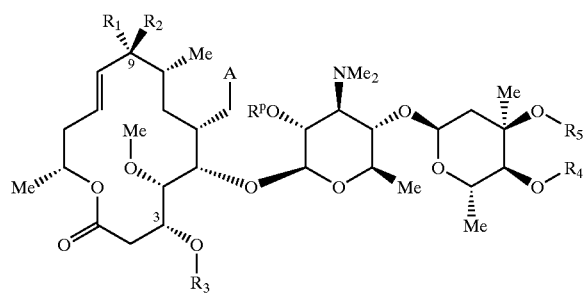

-continued

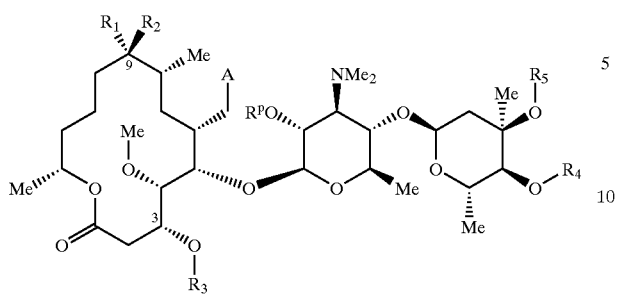

(III)

wherein,

A is:
(1) CHO;
(2) CH$_2$-X, where X is selected from the group consisting of
   a. hydroxy or protected hydroxy,
   b. halogen,
   c. NR7R8 wherein R7 and R8 are each independently selected from hydrogen and C1–C6-alkyl, optionally substituted with aryl or heterocyclic groups; or R7and R8 taken together with the nitrogen atom to which they are connected form a 3- to 7-membered ring which, may optionally contain a hetero function selected from the group consisting of —O—, —NH—, —N(C1–C6-alkyl)-, —N(aryl)-, —N(heteroaryl)- , —S—, —S(O)—and —S(O)2-,
   d. NR7C(O)—R9, where R7 is as previously defined and R9 is selected from the group consisting of
      i. C1–C6-alkyl, optionally substituted with aryl, substituted aryl, heterocyclic or substituted heterocyclic,
      ii. aryl,
      iii. substituted aryl,
      iv. heterocyclic, and
      v. substituted heterocyclic
   e. S(O)$_n$—(C1–C6-alkyl), optionally substituted with aryl or a heterocyclic group where n=0, 1 or 2,
   f. S(O)$_n$-(aryl or heterocyclic group) where n=0, 1 or 2, and
   g. O-(aryl or heterocyclic group);
(3) an aldehyde protecting group,
(4) substituted or unsubstituted imidazole, arylimidazole or heteroarylimidazole,
(5) substituted or unsubstituted oxazole, aryloxazole or heteroaryloxazole,
(6) substituted or unsubstituted thioxazole, arylthioxazole or heteroarylthioxazole,
(7) substituted or unsubstituted imidazoline, arylimidazoline or heteroarylimidazoline,
(8) substituted or unsubstituted oxazoline, aryloxazoline or heteroaryloxazoline, or
(9) substituted or unsubstituted thioxazoline, arylthioxazoline or heteroarylthioxazoline.

R1 and R2 are each independently selected from the group consisting of
(1) hydrogen,
(2) hydroxy,
(3) protected hydroxy,
(4) OC(O)—C1–C12 alkyl, optionally substituted with aryl, substituted aryl, heterocyclic, substituted heterocyclic,
(5) O—R7 where R7 is as previously defined,
(6) halogen, and
(7) R1 and P2 taken together are oxo;

R3, R4 and R5 are each independently selected from the group consisting of
(1) hydrogen,
(2) a hydroxy protecting group, and
(3) C(O)—C1–C12 -alkyl, optionally substituted with aryl, substituted aryl, heterocyclic, substituted heterocyclic, O—R7 or NR7R8 where R7 and NR7R8 are as previously defined; and R$^P$ is hydrogen or a hydroxy protecting group.

DETAILED DESCRIPTION OF THE INVENTION

A first embodiment of the invention is a compound represented by the Formula II as described above.

A second embodiment of the invention is a compound represented by the Formula III as described above.

Representative compounds of the invention are those selected from the group consisting of:

Compound of Formula II wherein A=CHO, R1=OH, R2=H, R3=Ac, R4=C(O)CH2CHMe2, R5=H, R$^P$=H;
Compound of Formula II wherein A=CHO, R1=OH, R2=H, R3=H, R4=C(O)CH2CHMe2, R5=H, R$^P$=H;
Compound of Formula II wherein A=CHO, R1=OH, R2=H, R3=H, R4=C(O)CH2CH2CH3, R5=H, R$^P$=H;
Compound of Formula II wherein A=CHO, R1=OH, R2=H, R3=H, R4=C(O)CH2CH3, R5=H, R$^P$=H;
Compound of Formula II wherein A=CHO, R1=OH, R2=H, R3=H, R4=C(O)CH3, R5=H, R$^P$=H;
Compound of Formula II wherein A=CHO, R1=OH, R2=H, R3=H, R4=H, R5=H, R$^P$=H;
Compound of Formula II wherein A=CHO, R1=OH, R2=H, R3=C(O)CH3, R4=C(O)CH2CH2CH3, R5=H, R$^P$=H;
Compound of Formula II wherein A=CHO, R1=OH, R2=H, R3=C(O)CH3, R4=C(O)CH2CH3, R5=H, R$^P$=H;
Compound of Formula II wherein A=CHO, R1=OH, R2=H, R3=C(O)CH3, R4=C(O)CH3, R5=H, R$^P$=H;
Compound of Formula II wherein A=CHO, R1=OH, R2=H, R3=C(O)CH3, R4=H, R5=H, R$^P$=H;
Compound of Formula II wherein A=CHO, R1=OAc, R2=H, R3=C(O)CH2CH3 R4=C(O)CH2CH2CH3, R5=Ac, R$^P$=H;
Compound of Formula II wherein A=CHO, R1=OH, R2=H, R3=H, R4=C(O)CH2CH3, R5=C(O)CH2CH3, R$^P$=H;
Compound of Formula II wherein A=CH2Br, R1=OH, R2=H, R3=Ac, R4=C(O)CH2CHMe2, R5=H, R$^P$=H;
Compound of Formula II wherein A=CH2F, R1=OH, R2=H, R3=Ac, R4=C(O)CH2CHMe2, R5=H, R$^P$=H;
Compound of Formula II wherein A=CH2NMe(Bn), R1=OH, R2=H, R3=Ac, R4=C(O)CH2CHMe2, R5=H, R$^P$=H;
Compound of Formula II wherein A=CH(OMe)2, R1=OH, R2=H, R3=Ac, R4=C(O)CH2CHMe2, R5=H, R$^P$=H;
Compound of Formula II wherein A=CH2OH, R1=OBn, R2=H, R3=Ac, R4=C(O)CH2CHMe2, R5=H, R$^P$=H;
Compound of Formula II wherein A=CHNOPh, R1=OH, R2=H, R3=Ac, R4=C(O)CH2CHMe2, R5=H, R$^P$=H;
Compound of Formula II wherein A=CHNOCH2CH3, R1=OH, R2=H, R3=Ac R4=C(O)CH2CHMe2, R5=H, R$^P$=H;
Compound of Formula II wherein A=CHNOCH3, R1=OH, R2=H, R3=Ac, R4=C(O)CH2CHMe2, R5=H, R$^P$=H;
Compound of Formula II wherein A=CHNOH, R1=OH, R2=H, R3=Ac, R4=C(O)CH2CHMe2, R5=H, R$^P$=H;

Compound of Formula II wherein A=CH2OH, R1=OH, R2=H, R3=Ac, R4=C(O)CH2CHMe2, R5=H, $R^P$=H;
Compound of Formula III wherein A=CHO, R1=OH, R2=H, R3=Ac R4=C(O)CH2CHMe2, R5=H, $R^P$=H;
Compound of Formula III wherein R1=CH2OH, R1=OH, R2=H, R3=Ac R4=C(O)CH2CHMe2, R5=H, $R^P$=H;
Compound of Formula II wherein A=CHO, R1=OAc, R2=H, R3=Ac, R4=C(O)CH2CHMe2, R5=H, $R^P$=H;
Compound of Formula II wherein A=CHO, R1=OC(O) CH2CH2C(O)OH, R2=H, R3=Ac, R4=C(O) CH2CHMe2, R5=H, $R^P$=H;
Compound of Formula II wherein A=CHO, R1=OC(O)Ph, R2=H, R3=Ac, R4=C(O)CH2CHMe2, R5=H, $R^P$=H;
Compound of Formula II wherein A=CH2[(4-methyl)-1-piperazinyl], R1=OH, R2=H, R3=Ac, R4=C(O) CH2CHMe2, R5=H, $R^P$=H;
Compound of Formula II wherein A=CH2[(4-phenyl)-1-piperazinyl], R1=OH, R2=H, R3=Ac, R4=C(O) CH2CHMe2, R5=H, $R^P$=H;
Compound of Formula II wherein A=CH2NMe2, R1=OH, R2=H, R3=Ac, R4=C(O)CH2CHMe2, R5=H, $R^P$=H;
Compound of Formula II wherein A=CHO, R1 and R2=O, R3=Ac, R4=C(O)CH2CHMe2, R5=H, $R^P$=H;
Compound of Formula II wherein A=CHNNH2, R1=OH, R2=H, R3=Ac, R4=C(O)CH2CHMe2, R5=H, $R^P$=H;
Compound of Formula II wherein A=CHNNMe2, R1=OH, R2=H, R3=Ac R4=C(O)CH2CHMe2, R5=H, $R^P$=H;
Compound of Formula II wherein A=CH=N—(N-morpholine), R1=OH, R2=H, R3=Ac, R4=C(O) CH2CHMe2, R5=H, $R^P$=H;
Compound of Formula II wherein A=CH(OMe)2, R1=H, R2=OH, R3=Ac R4=C(O)CH2CHMe2, R5=H, $R^P$=H;
Compound of Formula III wherein A=CH(OMe)2, R1=H, R2=OH, R3=Ac R4=C(O)CH2CHMe2, R5=H, $R^P$=H;
Compound of Formula II wherein A=CH(OMe)2, R1=Cl, R2=H, R3=Ac R4=C(O)CH2CHMe2, R5=H, $R^P$=H;
Compound of Formula II wherein A=CHO, R1=H, R2=OH, R3=Ac R4=C(O)CH2CHMe2, R5=H, $R^P$=H;
Compound of Formula II wherein A=CH(OMe)2, R1=H, R2=OH, R3=Ac R4=C(O)CH2CHMe2, R5=H, $R^P$=H;
Compound of Formula III wherein A=CHO, R1=H, R2=OH, R3=Ac R4=C(O)CH2CHMe2, R5=H, $R^P$=H;
Compound of Formula II wherein A=CH(OMe)2, R1=H, R2=OAc, R3=Ac R4=C(O)CH2CHMe2, R5=H, $R^P$=H; and
Compound of Formula III wherein A=CHO, R1 and R2=O, R3=Ac, R4=C(O)CH2CHMe2, R5=H, $R^P$=H;

Definitions

The terms "$C_1$–$C_3$-alkyl" or "$C_1$–$C_6$-alkyl" as used herein refer to saturated, straight- or branched-chain hydrocarbon radicals containing between one and three or one and six carbon atoms, respectively. Examples of $C_1$–$C_3$ alkyl radicals include methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl.

The term "$C_1$–$C_6$-alkoxy" as used herein refers to a $C_1$–$C_6$-alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkyl-amino" as used herein refers to one or two $C_1$–$C_3$-alkyl groups, as previously defined, attached to the parent molecular moiety through a nitrogen atom. Examples of $C_1$–$C_3$-alkyl-amino include, but are not limited to methylamino, dimethylamino, ethylamino, diethylamino and propylamino.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "aryl" as used herein refers to unsubstituted carbocyclic aromatic groups including, but not limited to, phenyl, 1- or 2-naphthyl and the like.

The term "$C_3$–$C_5$-cycloalkyl- and $C_3$–$C_7$-cycloalkyl" as used herein refers to carbocyclic groups of 3 to 5 or 3 to 7 carbons, respectively, for example, cyclopropyl, cyclobutyl, cyclopentyl, cyclohexyl, and cycloheptyl.

The term "$C_1$–$C_3$-alkyl-$C_3$–$C_5$-cycloalkyl", as used herein refers to a $C_3$–$C_5$-cycloalkyl radical, as defined above, attached to a $C_1$–$C_3$-alkyl radical by replacement of a hydrogen atom on the latter.

The terms "halo" and "halogen" as used herein refer to an atom selected from fluorine, chlorine, bromine and iodine.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl" as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic" as used herein, refers to heterocycloalkyl and heteroaryl. The term "substituted heterocyclic" as used herein, refers to substituted heterocycloalkyl and substituted heteroaryl.

"Hydroxy-protecting group", as used herein, refers to an easily removable group which is known in the art to protect a hydroxy group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis.* 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the Techniques of Chemistry Series, John Wiley & Sons, NY, 1986.

The term "substituted aryl" as used herein refers to an aryl group as defined herein substituted by independent replacement of one, two or three of the hydrogen atoms thereon with F, Cl, Br, I, OH, $NO_2$, CN, $C(O)$—$C_1$–$C_6$-alkyl, $C(O)$-aryl, $C(O)$-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, $OC(O)$—$C_1$–$C_6$-alkyl, $OC(O)$-aryl, $OC(O)$-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, $NHC(O)$—$C_1$–$C_6$-alkyl, $NHC(O)$-aryl, $NHC(O)$-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $S_2$—$C_1$–$C_6$-alkyl, $SO_2$-aryl, $SO_2$-heteroaryl, $SO_2NH_2$, $SO_2NH$—$C_1$–$C_6$-alkyl, $SO_2$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heteroaryl" as used herein refers to a heteroaryl group as defined herein substituted by independent replacement of one, two or three of the hydrogen atoms thereon with F, Cl, Br, I, OH, $NO_2$, CN, $C(O)$—$C_1$–$C_6$-alkyl, $C(O)$-aryl, $C(O)$-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, $OC(O)$—$C_1$–$C_6$-alkyl, $OC(O)$-aryl, $OC(O)$-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, $NHC(O)$—$C_1$–$C_6$-alkyl, NHC(O)-aryl, $NHC(O)$-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heterocycloalkyl" as used herein, refers to a heterocycloalkyl group, as defined above, substituted by independent replacement of one, two or three of the hydrogen atoms thereon with F, Cl, Br, I, OH, $NO_2$, CN, $C(O)$—$C_1$–$C_6$-alkyl, $C(O)$-aryl, $C(O)$-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, $OC(O)$—$C_1$–$C_6$-alkyl, $OC(O)$-aryl, $OC(O)$-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, $NHC(O)$—$C_1$–$C_6$-alkyl, $NHC(O)$-aryl, $NHC(O)$-heteroaryl, $NHCO_2$-alkyl, NHCO2-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyates, acrylates and ethylsuccinates.

The term "pharmaceutically acceptable prodrugs", as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable risk/reward ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel Delivery Systems,* Vol. 14 of the A.C.S. Symposium Series and in Edward B. Roche, ed., *Bioreversible Carriers in Drug Design,* American Pharmaceutical Association and Pergamon Press, 1987, both of which are incorporated by reference herein.

Antibacterial Activity

Susceptibility tests can be used to quantitatively measure the in vitro activity of an antimicrobial agent against a given bacterial isolate. Compounds were tested for in vitro antibacterial activity by a microdilution method. Minimal Inhibitory Concentration (MIC) was determined in 96 well microtiter plates utilizing the appropriate Mueller Hinton Broth medium (CAMHB) for the observed bacterial isolate. Antimicrobial agents were serial diluted (2-fold) in DMSO to produce a concentration range of 32 ug/ml to 0.0625 ug/ml. The diluted compounds (2 ul/well) were then transferred into sterile, uninoculated CAMHB (0.2 mL) by use of a 96-fixed tip pipetting station. The inoculum for each bacterial strain was standardized to $5 \times 10^5$ CFU/mL by optical comparison to a 0.5 McFarland turbidity standard. The plates were inoculated with 10 ul/well of adjusted bacterial inoculum. The 96 well plates were covered and incubated at 35+/−2° C. for 20–24 hours in an ambient air environment. Following incubation, plate wells were visually examined by Optical Density measurement for the presence of growth (turbidity). The lowest concentration of an antimicrobial agent at which no visible growth occurs was defined as the MIC.

Antibiotic control standards were included in alternate wells of the same 96 well plate as the antimicrobial agent of interest for testing. The selected control agent was chosen as a compound belonging to the same antibiotic class as the test compound and having known susceptibility patterns for the bacterial organism being tested.

All in vitro testing followed the guidelines described in the Approved Standards M7-A4 protocol published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment of from about 10 mg to about 1000 mg of the compound(s) of this invention per day in single or multiple doses.

Abbreviations

Abbreviations which have been used in the descriptions of the scheme and the examples that follow are: AIBN for azobisisobutyronitrile; Bu$_3$SnH for tributyltin hydride; CDI for carbonyldiimidazole; DBU for 1,8-diazabicyclo[5.4.0]undec-7-ene; DEAD for diethylazodicarboxylate; DMF for dimethyl formamide; DPPA for diphenylphosphoryl azide; EtOAc for ethyl acetate; MeOH for methanol; NaN(TMS)$_2$ for sodium bis(trimethylsilyl)amide; NMO for N-methylmorpholine N-oxide; TEA for triethylamine; THF for tetrahydrofuran; TPP for triphenylphosphine; DMAP for 4-N,N- dimethylamino-purine; and TFA for trifluoroacetic acid.

Synthetic Methods

The compounds and processes of the present invention will be better understood in connection with the following synthetic schemes which illustrate the methods by which the compounds of the invention may be prepared. The groups A, R1, R2, R3, R4, and R$^P$ are as defined above unless otherwise noted below.

Scheme 1

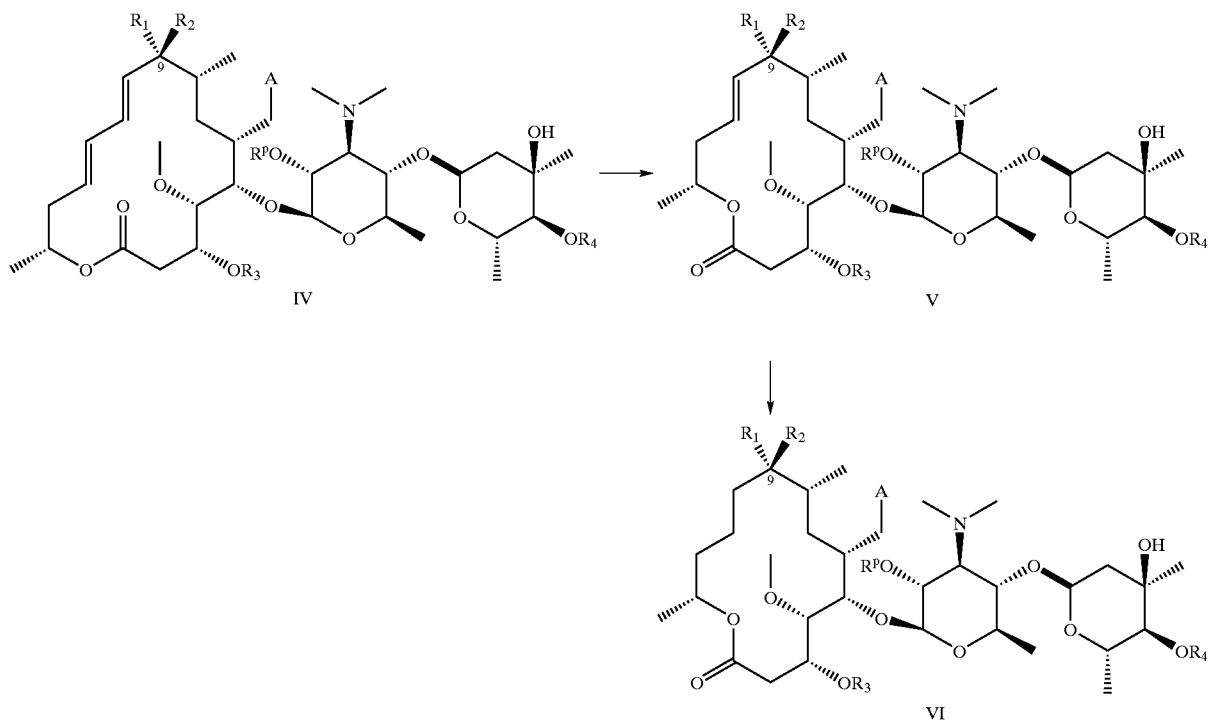

Process I

The process of the invention for the preparation of the compounds of Formula II comprises reacting a compound of Formula IV with Grubbs' ruthenium alkylidene or benzylidene catalysts (see (a) U.S. Pat. No. 6,111,121. (b) Reviews: *Synlett.* 1999, 2, 267 (c) Reviews: Ivin, K. J.; Mol. J. C. *Olefin Metathesis and Metathesis Polymerization*, 2$^{nd}$ ed.; Academic Press: New York, 1997. (d) *J. Org. Chem.* 1999, 64, 4798–4816. (e) *Angew. Chem., Int. Ed. Engl.* 1997, 36, 2036–2056. (f) *Tetrahedron* 1998, 54, 4413–4450) or Nolan's ruthenium catalyst (see (a) International Patent Application No. PCT/US99/20629; International Publication No. WO 00/15339; (b) *Org. Lett.* 2000, 2, 1517–1519. (c) *J. Org. Chem.* 2000, 65, 2204–2207.) or molybdenum catalysts (see (a) *J. Am. Chem. Soc.* 1990, 112, 3875. (b) *J. Am. Chem. Soc.* 1996, 118, 10926–10927.) optionally in the presence of additives such as ethylene, 1-hexene, isobutylene, titanium (IV) isopropoxide or aluminum (III) isopropoxide in an organic solvent such as dichlomethane, chloroform, toluene, benzene, THF, DMF and the like at from room temperature to 100° C. for 1–7 days to provide a 14-membered ring contracted product of Formula II (such as Formula V). The preferred ruthenium catalysts are Nolan's catalyst (tricyclohexylphosphine [1,3-bis(2,4,6-trimethylphenyl)-imidazol-2-ylidene] benzylidene Ruthenium (IV) dichloride) or tricyclohexylphosphine [1,3-bis(2, 4,6-trimethylphenyl)-4,5-dihydroimidazol-2-ylidene] benzylidene Ruthenium (IV) dichloride and the preferred solvent is dichlomethane or toluene.

Process II

Compounds of Formula II where A is CHO can be further derivatized to amino derivatives via reductive amination methods by treating with an amine compound in the presence of sodium borohydride or sodium cyanoborohydide and the like in an alcoholic solvent such as methanol, ethanol, or isopropanol at a pH of 2–6. Compounds of Formula II (such as Formula V) where A is CHO can be further reduced to a corresponding alcohol where A is —CH$_2$OH with various hydride reducing agents such as sodium borohydrides, lithium borohydrides, and the like. Compounds of Formula II (such a Formula V) can be further converted to compounds of Formula III (such as Formula VI) via hydrogenolysis methods such as treating compounds of Formula II with palladium catalysts (palladium black, palladium on carbon, RhCl(PPh$_3$)$_3$ and the like) in the presence of 1–4 atmospheres of hydrogen gas in an organic solvent such as methanol, ethanol, isopropanol, ethylacetate, DMF, and the like at from room temperature to about 60° C. for 1 hour to 2 days.

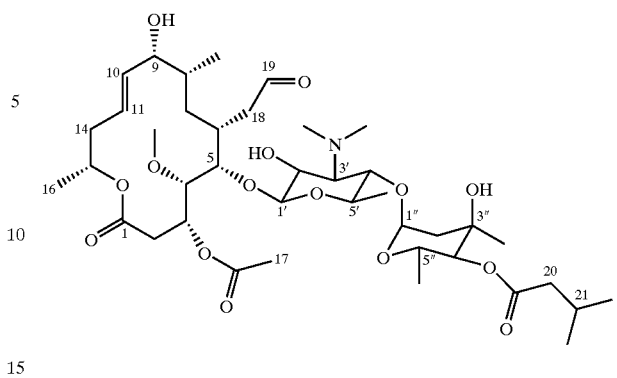

Partial proton and carbon NMR assignments in D2O/DMSO (20/80):

| Site | H | C |
|---|---|---|
| 2a | 2.96 | 38.6 |
| 2b | 3.35 | |
| 3 | 5.73 | 71.8 |
| 4 | 4.06 | 84.3 |
| 4-OMe | 4.04 | |
| 5 | 4.26 | 77.6 |
| 6 | 2.53 | 30.3 |
| 7a | 1.72 | 29.6 |
| 7b | 1.81 | |
| 8 | 2.25 | 35.5 |
| 8-Me | 1.52 | 16.4 |
| 9 | 4.46 | 72.8 |
| 10 | 6.11 | 131.6 |
| 11 | 6.41 | 130.8 |
| 14a | 2.84 | 38.8 |
| 14b | 3.08 | |
| 15 | 5.37 | 71.4 |
| 16-Me | 1.87 | 19.9 |
| 18a | 3.45 | 43.2 |
| 18b | 3.09 | |
| 19 | 10.2 | |
| 20 | 2.47 | 41.5 |
| 21 | 2.62 | 25.6 |
| 21-Me | 1.53 | |
| 1' | 4.94 | 103.8 |
| 2' | 3.88 | |
| 4" | 4.01 | |
| 5" | 4.94 | |
| 5"-Me | 1.66 | |

EXAMPLES

The procedures described above for preparing the compounds of the present invention will be better understood in connection with the following examples, which are intended to be illustrative only and not limiting of the scope of the invention. Various changes and modifications to the disclosed embodiments will be apparent to those skilled in the art. Such changes and modifications, including without limitation, those relating to the chemical structures, substituents, derivatives, intermediates, syntheses, formulations and/or methods of the invention may be made without departing from the spirit of the invention and the scope of the appended claims.

Example 1

Compound of Formula II: A=CHO, R1=OH, R2=H, R3=Ac, R4=C(O)CH2CHMe2, R5=H, R$^P$=H To a solution of Josamycin (5 g, 6.1 mmol) in dichloromethane (40 ml) there were added Nolan catalyst (see International Patent Application Publication No. WO 00/15339) (1.05 g, 1.21 mmol) and 1-hexene (1.53 ml, 12.2 mmol) and the reaction mixture was heated at reflux for 30 h. Afterwards, the crude mixture was concentrated in vacuo and combined with 2 g crude product from another run. The crude product was dissolved in a minimum amount of ethyl ether and was precipitated by a slow addition of hexane (6001). The orange solid was collected by filtration, dissolved in ethyl acetate and extracted with 10% NaHSO3. The aqueous extracts were basified with 1N NaOH to pH 8 and re-extracted with ethyl acetate. The combined organic extracts were dried over MgSO4 and concentrated in vacuo to give an off-white solid. The solid was dissolved in dichloromethane and stirred for 30 min with activated charcoal. After filtration and concentration in vacuo, the pure product was obtained as a white solid (3 g, 44% yield) MS (ESI) m/z: 802 (M+H)$^+$.

$^{13}$C NMR (100 MHz, CDCl$_3$): δ201.4, 173.1, 171.2, 170.1, 130.8, 123.1, 103.7, 97.7, 85.2, 76.0, 73.1, 71.6, 71.1, 70.8, 69.5, 68.9, 63.7, 62.3, 43.4, 42.1, 41.8, 39.0, 34.9, 25.7, 25.5, 22.6, 22.5, 21.2, 19.9, 18.9, 18.0.

Example 2

Compound of Formula II: A=CHO, R1=OH, R2H, R3=H, R4=C(O)CH2CHMe2, R5=H, R$^P$=H

The title compound of Example 2 was made by treating the compound of Example 1 with potassium carbonate in methanol at room temperature for 20 minutes.

MS m/z 761 (M+H)$^+$, $^{13}$C NMR (100 MHz, CDCl$_3$), δ203.0, 173.1, 17.03, 132.8, 129.9, 97.1, 75.7, 73.3, 71.3, 70.3, 69.5, 68.8, 63.6, 61.6, 60.5, 44.9, 43.4, 42.1, 41.8, 41.6, 39.3, 35.6, 32.4, 31.1, 30.6, 25.7, 25.5, 22.6, 22.5, 20.6, 19.2, 18.0, 16.6.

The title compound of Example 2 can also be prepared from leucomycin A1 (6.1 mmol), Nolan's catalyst (1.21 mmol) and 1-hexene in methylene chloride according to the procedures described in Example 1.

Example 3
Compound of Formula II: A=CHO, R1=OH, R2=H, R3=H, R4=C(O)CH2CH2CH3, R5=H, $R^P$=H The title compound of Example 3 was prepared by adding 1-hexene (82 μL, 0.65 mmol) and Nolan's catalyst (169 mg, 0.19 mmol) to a solution of kitasamycin (Leucomycin A5) (500 mg, 0.65 mmol in 30 ml of dichloromethane. The reaction mixture was brought to reflux and stirred for 3 days. The reaction mixture was monitored by mass spectroscopy and NMR spectroscopy. An additional 15% of catalyst (85 mg, 0.09 mmol) was added followed by the addition of 1-hexene (41 mL, 32 mmol) and the reaction mixture was stirred for one more day.

The solvent was evaporated in vacuo and the resulting foam was purified by column chromatography to provide the title compound. A gradient of solvent was used for purification: 1. hexane 2. methylene chloride 3.5% methanol, methylene chloride.

MS (ESI) m/z: 746.8 (M+H)$^+$, $^{13}$C NMR (100 MHz, CDCl$_3$), δ203.1, 173.7, 170.4, 133.0, 129.34, 105.7, 97.0, 75.6, 73.2, 71.8, 71.3, 71.2, 70.3, 69.7, 69.5, 69.5, 68.8, 63.5, 61.9, 61.6, 44.8, 421, 41.8, 39.3, 36.3, 35.7, 31.9, 31.1, 30.6, 27.7, 27.1, 27.0, 26.4, 26.2, 25.4, 20.5, 19.4, 19.2, 19.1, 19.0, 17.9, 16.6, 14.0, 13.8.

Example 4
Compound of Formula II: A=CHO, R1=OH, R2=H, R3=H, R4=C(O)CH2CH3, R5=H $R^P$=H The title compound of Example 4 is prepared from leucomycin A7 (6.1 mmol), Nolan's catalyst (1.21 mmol) and 1-hexene in methylene chloride according to the procedures described in Example 1.

Example 5
Compound of Formula II: A=CHO, R1=OH, R2=H, R3=H, R4=C(O)CH3, R5=H, $R^P$=H The title compound of Example 5 is prepared from leucomycin A9 (6.1 mmol), Nolan's catalyst (1.21 mmol) and 1-hexene in methylene chloride according to the procedures described in Example 1.

Example 6
Compound of Formula II: A=CHO, R1=OH, R2=H, R3=H, R4=H, R5=H, $R^P$=H The title compound of Example 6 is prepared from leucomycin V (A11) (6.1 mmol), Nolan's catalyst (1.21 mmol) and 1-hexene in methylene chloride according to the procedures described in Example 1.

Alternatively, the title compound was obtained by treating the compound of Example 1 with potassium carbonate in ethylene glycol at 100° C.

MS (ESI) m/z: 676 (M+H)$^+$

Example 7
Compound of Formula II: A=CHO, R1=OH, R2=H, R3=C(O)CH3, R4=C(O)CH2CH2CH3, R5=H, $R^P$=H The title compound of Example 7 is prepared from leucomycin A4 (6.1 mmol), Nolan's catalyst (1.21 mmol) and 1-hexene in methylene chloride according to the procedures described in Example 1.

Example 8
Compound of Formula II: A=CHO, R1=OH, R2=H, R3=C(O)CH3, R4=C(O)CH2CH3, R5=H, $R^P$=H The title compound of Example 8 is prepared from leucomycin A6 (6.1 mmol), Nolan's catalyst (1.21 mmol) and 1-hexene in methylene chloride according to the procedures described in Example 1.

Example 9
Compound of Formula II: A=CHO. R1=OH, R2=H, R3=C(O)CH3, R4=C(O)CH3, R5=H, $R^P$=H The title compound of Example 9 is prepared from leucomycin A8 (6.1 mmol), Nolan's catalyst (1.21 mmol) and 1-hexene in methylene chloride according to the procedures described in Example 1.

Example 10
Compound of Formula II: A=CHO, R1=OH, R2=H, R3=C(O)CH3, R4=H, R5=H, $R^P$=H The title compound of Example 10 is prepared from leucomycin U (6.1 mmol), Nolan's catalyst (1.21 mmol) and 1-hexene in methylene chloride according to the procedures described in Example 1.

Example 11
Compound of Formula II: A=CHO, R1=OAc, R2=H, R3=C(O)CH2CH3, R4=C(O)CH2CH2CH3, R5=Ac, $R^P$=H The title compound of Example 11 is prepared from leucomycin Miokamycin[1] (6.1 mmol), Nolan's catalyst (1.21 mmol) and 1-hexene in methylene chloride according to the procedures described in Example 1.

Example 12
Compound of Formula II: A=CHO, R1=OH, R2=H, R3=H, R4=C(O)CH2CH2CH3, R5=C(O)CH2CH3, $R^P$=H The title compound of Example 12 is prepared from leucomycin Rokitamycin[2] (6.1 mmol), Nolan's catalyst (1.21 mmol) and 1-hexene in methylene chloride according to the procedures described in Example 1.

Example 13
Compound of Formula II: A=CH$_2$Br, R1=OH, R2=H, R3=Ac, R4=C(O)CH2CHMe2, R5=H, $R^P$=H The title compound of Example 13 is prepared from the compound of Formula Ia where A=CH$_2$Br, R1=OH, R2=H, R3=Ac, R4=C(O)CH2CHMe2, Nolan's catalyst and 1-hexene in methylene chloride according to the procedures described in Example 1.

Example 14
Compound of Formula II: A CH$_2$F, R1=OH, R2=H, R3=Ac, R4=C(O)CH2CHMe2, R5=H, $R^P$H The title compound of Example 14 is prepared from the compound of Formula Ia where A=CH$_2$F, R1=OH, R2=H, R3=Ac, R4=C(O)CH2CHMe2, Nolan's catalyst and 1-hexene in methylene chloride according to the procedures described in Example 1.

Example 15
Compound of Formula II: A=CH2NMe(Bn), R1=OH, R2=H, R3=Ac, R4=C(O)CH2CHMe2, R5=H, $R^P$=H The title compound of Example 15 is prepared from the compound of Formula Ia where A=CH2NMe(Bn), R1=OH, R2=H, R3=Ac, R4=C(O)CH2CHMe2, Nolan's catalyst and 1-hexene in methylene chloride according to the procedures described in Example 1.

Example 16
Compound of Formula II: A=CH(OMe)2, R1=OH, R2=H, R3=Ac, R4=C(O)CH2CHMe2, R5=H, $R^P$=H The title compound of Example 16 is prepared from the compound of Formula Ia where A=CH(OMe)2, R1=OH, R2=H, R3=Ac, R4=C(O)CH2CHMe2, Nolan's catalyst and 1-hexene in methylene chloride according to the procedures described in Example 1.

Example 17
Compound of Formula II: A=CH2OH, R1=OBn, R2=H, R3=Ac, R4=C(O)CH2CHMe2, R5=H, $R^P$=H The title compound of Example 17 is prepared from the compound of Formula Ia where A=CH2OH, R1=OBn, R2=H, R3=Ac, R4=C(O)CH2CHMe2, Nolan's catalyst and 1-hexene in methylene chloride according to the procedures described in Example 1.

Example 18
Compound of Formula II: A=CHNOPh, R1=OH, R2=H, R3=Ac, R4=C(O)CH2CHMe2, R5=H, $R^P$H To a solution of the compound of Example 1 (200 mg, 0.24 mmol) in methanol (5 mL) there were added phenylhydroxylamine hydrochloride (35 mg, 0.24 mmol) and sodium acetate (20 mg, 0.24 mmol). The reaction mixture was heated to reflux for two hours and afterwards was concentrated to dryness. The crude mixture was diluted with ethyl acetate and washed with brine. Purification by flash chromatography (silica gel, 30/1 methylene choloride/methanol) afforded the pure product as a white solid (70 mg, 33% yield).

MS (ESI) m/z 893 (M+H)$^+$

Example 19
Compound of Formula II A=CHNOCH2CH3, R1=OH, R2=H, R3=Ac, R4=C(O)CH2CHMe2, R5=H, $R^P$=H To a solution of the compound of Example 1 (100 mg, 0.12 mmol) in methanol (5 mL) there were added ethylhydroxylamine hydrochloride (11 mg, 0.12 mmol) and sodium acetate (10 mg, 0.12 mmol). The reaction mixture was heated to reflux for two hours and afterwards was concentrated to dryness. The crude mixture was diluted with ethyl acetate and washed with brine. Purification by flash chromatography (silica gel, 30/1 methylene choloride/methanol) afforded the pure product as a white solid (50 mg, 49% yield).

MS (ESI) m/z: 845 (M+H)$^+$

Example 20
Compound of Formula II: A=CHNOCH3, R1=OH, R2=H, R3=Ac R4=C(O)CH2CHMe2, R5=H, $R^P$=H To a solution of the compound of Example 1 (300 mg, 0.36 mmol) in methanol (5 mL) there were added methylhydroxylamine hydrochloride (33 mg, 0.36 mmol) and sodium acetate (30 mg, 0.36 mmol). The reaction mixture was heated to reflux for two hours and afterwards was concentrated to dryness. The crude mixture was diluted with ethyl acetate and washed with brine. Purification by flash chromatography (silica gel, 30/1 methylene choloride/methanol) afforded the pure product as a white solid (150 mg, 50% yield).

MS (ESI) m/z: 831 (M+H)$^+$

Example 21
Compound of Formula II: A=CHNOH, R1=OH, R2=H, R3=Ac R4=C(O)CH2CHMe2, R5=H, $R^P$=H To a solution of the compound of Example 1 (100 mg, 0.12 mmol) in methanol (5 mL) there were added hydroxylamine hydrochloride (8.7 mg, 0.12 mmol) and sodium acetate (10 mg, 0.12 mmol). The reaction mixture was heated to reflux for two hours and afterwards was concentrated to dryness. The crude mixture was diluted with ethyl acetate and washed with brine. Purification by flash chromatography (silica gel, 30/1 methylene choloride/methanol) afforded the pure product as a white solid (8 mg 8% yield).

MS (ESI) m/z: 817 (M+H)$^+$

Example 22
Compound of Formula II: A=CH2OH, R1=OH, R2=H, R3=Ac R4=C(O)CH2CHMe2, R5=H, $R^P$=H To a solution of the compound of Example 1 (250 mg, 0.3 mmol) in isopropanol and water (10 ml, 1/1) there was added sodium borohydride (3 mg, 0.07 mmol) and the reaction was stirred for four hours at ambient temperature. The reaction mixture was quenched with saturated sodium bicarbonate and the crude was extracted with methylene chloride. Purification by flash chromatography (silica gel, 30/1 methylene chloride/methanol) afforded the pure product as a white solid (75 mg, 31% yield).

MS (ESI) m/z: 804 (M+H)$^+$

Example 23
Compound of Formula III A=CHO R1=OH, R2=H R3=Ac R4=C(O)CH2CHMe2, R5=H, $R^P$=H A solution of the compound of Example 1, (100 mg, 0.12 mmol) and 10% mol platinum oxide in ethanol (3 ml) was placed under a hydrogen balloon and stirred at ambient temperature for 18 hours. Afterwards, the reaction was filtered, rinsed with ethanol and concentrated to dryness to afford the product as a white solid (76 mg, 79% yield).

MS (ESI) m/z: 804 (M+H)$^+$

Example 24
Compound of Formula III: A=CH2OH, R1=OH, R2=H, R3=Ac R4=C(O)CH2CHMe2, R5=H, $R^P$=H A solution of the compound of Example 22 (30 mg, 0.035 mmol)) and 10% mol platinum oxide in ethanol (3 ml) was placed under a hydrogen balloon and stirred at ambient temperature for 18 hours. Afterwards, the reaction was filtered, rinsed with ethanol and concentrated to dryness to afford the product as a white solid (20 mg, 71% yield).

MS (ESI) m/z: 806 (M+H)$^+$

Example 25
Compound of Formula II: A=CHO, R1=OAc, R1=H, R3=Ac R4=C(O)CH2CHMe2, R5=H, $R^P$=H To a solution of the compound of Example 1 (100 mg, 0.2 mmol) in methylene chloride (3 ml) there were added acetic anhydride (0.015 ml, 0.13 mmol), 4-methylmorpholine (0.012 ml, 0.13 mmol), and DMAP (1.4 mg, 0.013 mmol) and the reaction was stirred at ambient temperature for 18 hours. Afterwards, the mixture was diluted with ethyl acetate, washed with saturated sodium bicarbonate, brine, dried over magnesium sulfate, and concentrated. Purification by flash chromatography (silica gel, 30/1 methylene chloride/methanol) afforded the pure product as a clear oil (75 mg, 74% yield).

MS (ESI) m/z: 844 (M+H)$^+$

Example 26
Compound of Formula II: A=CHO, R1=OC(O)CH2CH2C(O)OH, R2=H, R3=Ac, R4=C(O)CH2CHMe2, R5=H, $R^P$=H To a solution of the compound of Example 1 (100 mg, 0.12 mmol) in methylene chloride (3 ml) there were added succinic anhydride (13 mg, 0.13 mmol), 4-methylmorpholine (0.012 ml, 0.13 mmol), and DMAP (1.4 mg, 0.013 mmol) and the reaction was stirred at ambient temperature for 18 hours. Afterwards, the mixture was diluted with ethyl acetate, washed with saturated sodium bicarbonate, brine, dried over magnesium sulfate, and concentrated. Purification by flash chromatography (silica gel, 30/1 methylene chloride/methanol) afforded the pure product as a clear oil (73 mg, 67% yield).

MS (ESI) m/z: 902 (M+H)$^+$

Example 27
Compound of Formula II: A=CHO, R1=OC(O)Ph, R2=H, R3=Ac R4=C(O)CH2CHMe2, R5=H, $R^P$=H To a solution of the compound of Example 1 (200 mg, 0.25 mmol) in methylene chloride (3 ml) there were added benzoic anhydride (62 mg, 0.28 mmol), 4-methylmorpholine (0.038 ml, 0.28 mmol), and DMAP (3.1 mg, 0.025 mmol) and the reaction was stirred at ambient temperature for 18 hours. Afterwards, the mixture was diluted with ethyl acetate, washed with saturated sodium bicarbonate, brine, dried over magnesium sulfate, and concentrated. Purification by flash chromatography (silica gel, 30/1 methylene chloride/methanol) afforded the pure product as a clear oil (49 mg, 23% yield).
MS (ESI) m/z: 906 (M+H)$^+$

Example 28
Compound of Formula II: A=CH2[(4-methyl)-1-piperazinyl], R1=OH, R2=H, R3=Ac, R4=C(O)CH2CHMe2, R5=H, $R^P$=H To a solution of the compound of Example 1 (75 mg, 0.094 mmol) in methanol (3 mL) there were added 4A molecular sieves and 1-methylpiperazine (0.027 ml, 0.188 mmol) and the reaction mixture was stirred for 30 min at ambient temperature. Afterwards sodium cyanoborohydride (23.6 mg, 0.376 mmol) was added and the reaction was stirred for an additional 1 hour. The reaction was then quenched with saturated sodium bicarbonate and extracted with methylene chloride. The organic extracts were washed with brine, dried over magnesium sulfate and concentrated to dryness. Purification by flash chromatography (silica gel, 9/1 methylene chloride/methanol, 2% Et3N) afforded the pure product as a white solid (11 mg, 13% yield).
MS (ESI) m/z: 886 (M+H)$^+$

Example 29
Compound of Formula II: A=CH2[(4-phenyl)-1-piperazinyl], R1=OH, R2=H, R3=Ac, R4=C(O)CH2CHMe2, R5=H, $R^P$=H To a solution of the compound of Example 1 (95 mg, 0.118 mmol) in methanol (3 mL) there were added 4A molecular sieves and 1-phenylpiperazine (0.036 ml, 0.236 mmol) and the reaction mixture was stirred for 30 min at ambient temperature. Afterwards sodium cyanoborohydride (30.0 mg, 0.472 mmol) was added and the reaction was stirred for an additional 1 hour. The reaction was then quenched with saturated sodium bicarbonate and extracted with methylene chloride. The organic extracts were washed with brine, dried over magnesium sulfate and concentrated to dryness. Purification by flash chromatography (silica gel, 9/1 methylene chloride/methanol, 2% Et3N) afforded the pure product as a white solid (7 mg, 6% yield).
MS (ESI) m/z: 948 (M+H)$^+$

Example 30
Compound of Formula II: A=CH2NMe2, R1=OH, R2=H, R3=Ac R4 C(O)CH2CHMe2, R5=H, $R^P$=H To a solution of the compound of Example 1(95 mg, 0.118 mmol) in methanol (3 mL) there were added 4A molecular sieves and dimethylamine (2M in methanol, 0.118 ml, 0.234 mmol)) and the reaction mixture was stirred for 30 min at ambient temperature. Afterwards sodium cyanoborohydride (30.0 mg, 0.472 mmol) was added and the reaction was stirred for an additional 1 hour. The reaction was then quenched with saturated sodium bicarbonate and extracted with methylene chloride. The organic extracts were washed with brine, dried over magnesium sulfate and concentrated to dryness. Purification by flash chromatography (silica gel, 9/1 methylene chloride/methanol, 2% Et3N) afforded the pure product as a white solid (9 mg, 6% yield).
MS (ESI) m/z: 831 (M+H)$^+$

Example 31
Compound of Formula II: A=CHO, R1 and R2=O, R3=Ac R4=C(O)CH2CHMe2, R5=H, $R^P$=H To a solution of the compound of Example 1 (130 mg, 0.162 mmol) in methylene chloride (5 ml) there were added pyridinium chlorochromate (105 mg, 0.486 mmol) and sodium acetate (12.2 mg, 0.149 mmol) and the reaction mixture was stirred at ambient temperature for 18 hours. Afterwards the crude mixture was filtered and purified by flash chromatography (silica gel, 16/1 methylene chloride/methanol) to afford the pure product as a white solid (9 mg, 7% yield).
MS (ESI) m/z: 800 (M+H)$^+$

Example 32
Compound of Formula II: A=CHNNH2, R1=OH, R2=H, R3=Ac R4=C(O)CH2CHMe2, R5=H, $R^P$=H To a solution of the compound of Example 1 (100 mg, 0.125 mmol) in methanol (3 ml) there was added hydrazine (1M in THF, 0.0125 ml, 0.125 mmol) and the reaction was stirred at ambient temperature overnight. Afterwards the crude mixture was concentrated and purified by flash chromatography (silica gel, 9/1 methylene chloride/methanol, 1% Et3N) to afford the pure product as a white solid (8.7 mg, 9% yield).
MS (ESI) m/z: 816 (M+H)$^+$

Example 33
Compound of Formula II: A=CHNNMe2, R1=OH, R2=H, R3=Ac R4=C(O)CH2CHMe2, R5=H, $R^P$=H To a solution of the compound of Example 1 (200 mg, 0.249 mmol) in methanol (3 ml) there were added 3A molecular sieves and dimethylhydrazine (15 mg, 0.249 mmol) and the reaction was heated at reflux for 24 hours. Afterwards the crude mixture was diluted with ethyl acetate, washed with brine and dried over magnesium sulfate. After concentration to dryness and purification by flash chromatography (silica gel, 15/1 methylene chloride/methanol), the pure product was isolated as a white solid (19.1 mg, 19% yield).
MS (ESI) m/z: 844 (M+H)$^+$

Example 34
Compound of Formula II: A=CH=N-(N-morpholine), R1=OH, R2=H, R3=Ac, R4=C(O)CH2CHMe2, R5=H, $R^P$=H To a solution of the compound of Example 1 (200 mg, 0.249 mmol) in methanol (3 ml) there were added 3A molecular sieves and 4-aminomorpholine (25.4 mg, 0.249 mmol) and the reaction was heated at reflux for 24 hours. Afterwards the crude mixture was diluted with ethyl acetate, washed with brine and dried over magnesium sulfate. After concentration to dryness and purification by flash chromatography (silica gel, 20/1 methylene chloride/methanol), the pure product was isolated as a white solid (21.2 mg, 11% yield).
MS (ESI) m/z: 886 (M+H)$^+$

Example 35
Compound of Formula II: A=CH(OMe)2, R1=H, R2=OH, R3=Ac, R4=C(O)CH2CHMe2, R5=H, $R^P$=H
Step 35a. Compound of Formula IV: A=CHO, R1 and R2=O R3=Ac, R4=C(O)CH2CHMe2, $R^P$=H A solution of $CrO_3$ (7.0 g, 70 mmol) in water (7 mL) was added dropwise over 10 minutes to pyridine (30 mL) at 0°

C. To the CrO₃ mixture, a solution of josamycin (6.6 g, 7.98 mmol) in pyridine (15 mL) was added, and stirred for 2 hours at room temperature. The mixture was diluted with water and extracted with dichloromethane. The organic solution was dried over anhydrous sodium sulfate, and concentrated under vacuum. The residue was purified by chromatography on silica gel (eluting with 1:5 hexanes:ethyl acetate) to give the desired compound (2.87 g, 44%) as a white solid.

MS (ESI) m/z: 826 (M+H)⁺

$^{13}$C-NMR(100 MHz, CDCl₃): δ203.03, 201.00, 149.74, 144.35, 140.55, 136.33, 132.67, 129.14, 128.34, 125.42, 123.98, 122.35, 103.73, 97.13, 84.94, 77.80, 77.57, 77.12, 76.02, 72.99, 71.66, 69.47, 69.21, 68.82, 68.55, 63.58, 62.63, 44.34, 43.40, 43.03, 42.05, 41.77, 40.82, 36.85, 32.26, 30.88, 25.65, 25.47, 22.58, 22.52, 21.32, 20.61, 18.90, 17.97, 17.57.

Step 35b. Compound of Formula IV: A=CH(OMe)2, R1 and R2=O R3=Ac, R4=C(O)CH2CHMe2, $R^P$=Bz A solution of the compound from step 35a (1.37 g, 1.66 mmol), Bz₂O (1.0 g, 4.42 mmol) in pyridine (20 mL) was stirred overnight at room temperature. The solution was concentrated under vacuum, diluted with dichloromethane (80 mL), washed with aqueous sodium bicarbonate solution, and dried over anhydrous sodium sulfate. The solvent was evaporated, and the residue was dissolved in methanol (60 mL). The pH of the methanol solution was adjusted to 3 by adding acetic chloride at 0° C. The solution was stirred overnight, neutralized with sodium bicarbonate, and concentrated. Purification on silica gel chromatography (eluting with 5:1 toluene:acetone) gave compound 3 (1.52 g, 94%) as a light yellow solid.

MS (ESI) m/z: 976 (M+H)⁺

$^{13}$C-NMR(100 MHz, CDCl₃): δ203.94, 173.02, 170.10, 169.86, 164.41, 143.57, 139.65, 133.38, 132.99, 130.22, 129.85, 129.18, 128.76, 128.37, 125.45, 122.84, 100.61, 100.55, 97.15, 85.61, 77.52, 77.15, 75.84, 75.20, 72.94, 71.61, 69.55, 69.35, 68.95, 68.10, 63.60, 62.16, 54.16, 47.12, 44.32, 43.41, 41.94, 41.80, 40.45, 36.81, 33.10, 32.11, 29.73, 25.67, 25.46, 22.59, 22.54, 21.17, 20.61, 19.04, 18.11, 17.94.

Step 35c. Compound of Formula IV: A=CH(OMe)2, R1=H, R2=OH, R3=Ac, R4=C(O)CH2CHMe2, $R^P$=Bz To a mixture of the compound from step 35b (1.39 g, 1.43 mmol), CeCl₃ 7H₂O (531 mg, 1.43 mmol) in methanol (4 mL) there was added NaBH₄ (107.8 mg, 2.85 mmol) at −60° C. The mixture was stirred for 5 minutes, quenched with aqueous ammonium chloride solution, and extracted with dichloromethane. The organic solution was washed with aqueous sodium bicarbonate solution, dried over anhydrous sodium sulfate, and concentrated under vacuum. Purification with silica gel chromatography (eluting with 5:1 toluene:acetone) gave the desired compound (1.13 g, 82%) as a white solid.

MS (ESI) m/z: 978 (M+H)⁺

$^{13}$C-NMR(100 MHz, CDCl₃): δ173.01, 170.21, 170.12, 164.41, 133.30, 132.92, 131.36, 130.30, 130.01, 129.82, 129.38, 129.15, 128.71, 128.35, 125.44, 102.32, 100.46, 97.10, 85.50, 77.56, 77.13, 76.41, 75.94, 75.22, 72.95, 71.59, 69.60, 69.54, 69.19, 68.13, 63.58, 62.03, 52.56, 51.37, 43.40, 41.97, 41.78, 40.69, 36.75, 35.70, 32.45, 30.89, 30.15, 25.64, 25.44, 22.57, 22.52, 21.59, 21.32, 20.87, 20.40, 19.10, 18.10.

Step 35d. Compound of Formula II: A=CH(OMe)2, R1=H, R=OH, R3=Ac R4=C(O)CH2CHMe2, R5=H, $R^P$=Bz To a solution of the compound from step 35c (1.0 g, 1.02 mmol) in dichloromethane (50 mL) there was added Ti(O$^i$Pr)₄ (0.120 mL, 0.40 mmol) and refluxed for 20 minutes. The solution was cooled down to room temperature, degassed with nitrogen, and then Nolan catalyst (86 mg, 0.10 mmol) was added. The solution was stirred for 3 days at 50° C. under nitrogen, and concentrated under vacuum. Purification with silica gel chromatography (eluting with ethyl acetate) gave the desired compound (0.90 g, 92%) as a white solid.

MS (ESI) m/z: 952 (M+H)⁺

$^{13}$C-NMR(100 MHz, CDCl₃): δ173.03, 170.49, 168.88, 164.45, 135.60, 133.32, 130.27, 129.74, 129.15, 128.68, 128.35, 127.28, 125.43, 101.52, 100.69, 97.12, 78.44, 77.55, 77.13, 75.88, 72.94, 71.53, 70.24, 69.55, 68.10, 63.59, 61.78, 53.83, 43.40, 41.96, 41.78, 38.08, 37.66, 36.77, 35.26, 31.44, 25.64, 25.44, 22.57, 22.52, 21.11, 19.06, 18.41, 18.09.

Step 35e. Compound of Formula II: A=CH(OMe)2, R1=H, R2=OH, R3=Ac, R4=C(O)CH2CHMe2, R5=H, $R^P$=H The compound from step 35d is treated with methanol at reflux for 24 hours to give the title compound.

Example 36

Compound of Formula III: A=CH(OMe)2, R1=H, R2=OH, R3=Ac, R4=C(O)CH2CHMe2, R5=H, $R^P$=H Step 36 a. Compound of Formula VI: A=CH(OMe)2, R3=Ac, R4=C(O)CH2CHMe2, $R^P$=Bz A mixture of the compound from step 35d (0.54 g, 0.568 mmol) and Pd(OH)₂/C (50 mg) in methanol (30 mL) was stirred under H₂ (attached with a balloon) overnight. The catalyst was filtered off. The solvent was evaporated to give the desired compound (0.53 g, 98%) as white solid.

MS (ESI) m/z: 954 (M+H)⁺

$^{13}$C-NMR(100 MHz, CDCl₃): δ173.11, 170.50, 169.02, 164.54, 133.42, 130.27, 129.87, 128.80, 101.54, 100.72, 97.18, 77.43, 75.93, 75.37, 73.59, 72.96, 71.72, 70.01, 69.60, 68.03, 63.64, 61.94, 54.11, 48.79, 43.45, 42.02, 41.82, 37.01, 34.30, 34.09, 33.57, 32.88, 32.74, 25.70, 25.47, 22.61, 22.55, 21.11, 21.02, 19.94, 19.07, 18.13, 15.83.

Step 36b. Compound of Formula III: A=CH(OMe)2, R1=H, R2=OH, R3=Ac R4=C(O)CH2CHMe2, R5=H, $R^P$=H The compound from step 36a is treated with methanol at reflux for 24 hours to give the title compound.

Example 37

Compound of Formula II: A=CH(OMe)2, R1=Cl, R2=H, R3=Ac R4=C(O)CH2CHMe2, R5=H, $R^P$=H Step 37a. Compound of Formula II: A=CH(OMe), R1=Cl, R2=H, R3=Ac R4=C(O)CH2CHMe2, R5=H, $R^P$=Bz To a solution of the compound from step 35d (0.115 g, 0.121 mmol) in dichloromethane (10 mL) containing triethylamine (0.05 mL, 0.36 mmol) there was added MsCl (0.011 mL, 0.145 mmol) at 0° C. The solution was stirred overnight, washed with aqueous sodium bicarbonate, and dried over anhydrous sodium sulfate. The solvent was evaporated. Purification with silica gel chromatography (eluting with 3:1 ethyl acetate:hexane) gave the title compound (51 mg, 44%) as a white solid.

MS (ESI) m/z: 970 (M+H)⁺

$^{13}$C-NMR(100 MHz, CDCl₃): δ171.91, 169.48, 168.43, 163.31, 136.40, 132.22, 129.49, 129.02, 128.58, 127.54, 99.97, 99.67, 96.02, 85.37, 76.24, 75.49, 74.70, 71.73, 70.30, 69.43, 68.40, 67.02, 62.46, 60.96, 60.87, 59.62, 52.75, 47.43, 42.25, 40.75, 40.64, 30.62, 30.51, 24.50, 24.28, 21.41, 21.36, 19.85, 19.75, 19.56, 18.79, 17.84, 16.94.

Step 37b. Compound of Formula II: A=CH(OMe)2, R1=Cl, R2=H, R3=Ac R4=C(O)CH2CHMe2, R5=H, $R^P$=H The compound from step 37a is treated with methanol at reflux for 24 hours to give the title compound.

Example 38

Compound of Formula II: A=CHO, R1=H, R2=OH, R3=Ac R4=C(O)CH2CHMe2, R5=H, $R^P$=H Step 38a. Compound of Formula II A=CHO, R1=H, R2=OH, R3=Ac R4=C(O)CH2CHMe2, R5=H, $R^P$=Bz To a solution of the compound from step 35d (0.20 g, 0.21 mmol) in acetonitrile (3 mL) there were added water (15 mL) and TFA (0.048 mL, 0.63 mmol). The mixture was stirred overnight at room temperature, diluted with aqueous sodium bicarbonate and extracted with dichloromethane. The organic solution was dried over anhydrous sodium sulfate and concentrated under vacuum. Purification with silica gel chromatography (eluting with ethyl acetate) gave the desired compound (0.151 g, 80%) as a white solid.

MS (ESI) m/z: 906 (M+H)$^+$

Step 38b. Compound of Formula II: A=CHO, R1=H, R2=OH, R3=Ac R4=C(O)CH2CHMe2, R5=H, $R^P$H A solution of the compound from step 38a (0.15 g, 0.166 mmol) in methanol (30 mL) was refluxed for 3 days. The solvent was evaporated under vacuum. Purification with silica gel chromatography (eluting with ethyl acetate) gave the title compound (85.6 mg, 64%) as a white solid.

MS (ESI) m/z: 802 (M+H)$^+$ $^{13}$C-NMR(100 MHz, CDCl$_3$): δ201.79, 173.11, 171.45, 169.47, 133.96, 127.95, 103.99, 97.20, 92.03, 84.25, 78.63, 77.96, 77.44, 77.16, 76.07, 73.11, 71.68, 70.69, 70.34, 69.53, 68.88, 63.67, 62.16, 44.07, 43.46, 42.10, 41.83, 38.52, 37.88, 36.59, 32.89, 29.85, 25.70, 25.51, 22.61, 22.55, 21.30, 19.77, 19.29, 18.98, 18.00, 14.34, 14.28.

Example 39

Compound of Formula III: A=CH(OMe)2, R1=H, R2=OH, R3=Ac R4=C(O)CH2CHMe2, R5=H, $R^P$=H A solution of the compound from step 36a (0.20 g, 0.21 mmol) in methanol (30 mL) was refluxed for 3 days. The solvent was evaporated under vacuum to give the crude title compound.

MS (ESI) m/z: 850 (M+H)$^+$

Example 40

Compound of Formula III: A=CHO, R1=H, R2=OH, R3=Ac R4=C(O)CH2CHMe2, R5=H, $R^P$=H To a solution of the crude compound from Example 39 in acetonitrile (3 mL) there were added water (15 mL) and TFA (0.048 mL, 0.63 mmol). The mixture was stirred overnight at room temperature, diluted with aqueous sodium bicarbonate and extracted with dichloromethane. The organic solution was dried over anhydrous sodium sulfate and concentrated under vacuum. Purification with silica gel chromatography (eluting with ethyl acetate) gave the title compound (70 mg, 42% yield from the starting compound) as a white solid.

MS (ESI) m/z: 804 (M+H)$^+$ $^{13}$C-NMR(100 MHz, CDCl$_3$): δ201.70, 173.13, 171.61, 169.69, 97.23, 79.00, 77.44, 77.17, 76.10, 75.74, 74.68, 73.09, 71.71, 69.88, 69.54, 68.87, 63.69, 62.21, 45.42, 43.47, 42.12, 41.85, 38.46, 34.34, 32.71, 31.74, 29.86, 25.72, 25.52, 22.62, 22.57, 21.27, 20.45, 19.00, 18.01.

Example 41

Compound of Formula II: A=CH(OMe)2, R1=H, R2=OAc, R3=Ac R4=C(O)CH2CHMe2, R5=H, $R^P$=Ac Step 41a. Compound of Formula II: A=CH(OMe)2, R1=H, R2=OH, R3=Ac R4=C(O)CH2CHMe2, R5=H, $R^P$=Ac To a degassed solution of a compound of Formula IV: A=CH(OMe)2, R1=H, R2=OH, R3=Ac, R4=C(O)CH2CHMe2, $R^P$=Ac (2.57 g, 2.81 mmol) in dichloromethane (100 mL) there was added Nolan catalyst (0.50 g, 0.59 mmol) followed by l-hexene (0.70 mL, 5.62 mmol). The solution was stirred for 1 day at 50° C. under nitrogen, and concentrated under vacuum. Purification with silica gel chromatography (eluting with ethyl acetate) gave the title-compound (1.06 g, 43%) as white solid.

MS (ESI) m/z: 890 (M+H)$^+$ $^{13}$C-NMR(100 MHz, CDCl$_3$): δ173.04, 170.57, 169.13, 168.85, 100.56, 97.15, 78.45, 77.52, 77.13, 75.85, 72.81, 71.09, 70.45, 69.55, 68.08, 63.58, 61.63, 43.41, 41.80, 25.66, 25.41, 22.57, 22.52, 21.77, 21.13, 19.00, 18.78, 18.09.

Step 41b. Compound of Formula II: A=CH(OMe)2, R1=H, R2=OAc, R3=Ac, R4=C(O)CH2CHMe2, R5=H, $R^P$=Ac A solution of the compound from step 41a (0.23 g, 0.259 mmol), Ac$_2$O (1.5 mL) in pyridine (20 mL) was stirred overnight at room temperature. The solution was concentrated under vacuum, diluted with dichloromethane (80 mL), washed with aqueous sodium bicarbonate solution, and dried over anhydrous sodium sulfate. Purification with silica gel chromatography (eluting with ethyl acetate) gave the title compound (0.23 g, 96%).

MS (ESI) m/z: 932 (M+H)$^+$ $^{13}$C-NMR(100 MHz, CDCl$_3$): δ172.94, 170.60, 170.22, 168.96, 168.85, 100.59, 97.00, 79.39, 77.61, 76.97, 75.80, 72.78, 71.01, 70.31, 69.69, 67.86, 63.53, 61.52, 43.29, 41.70, 41.59, 25.56 25.28, 22.48, 22.43, 21.62, 21.22, 21.10, 21.06, 18.94, 18.61, 17.98.

Step 41c. Compound of Formula II: A=CH(OMe)2, R1=H, R2 OAc, R3=Ac R4=C(O)CH2CHMe2, R5=H, $R^P$H The compound from step 41b is treated with methanol at reflux for 24 hours to give the title compound.

Example 42

Compound of Formula III: A=CHO, R1 and R2=O, R3=Ac, R4=C(O)CH2CHMe2, R5=H, $R^P$=H The compound of Example 40 was converted to the title compound according to the procedure described in Example 31.

MS (ESI) m/z: 803 (M+H)$^+$

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by the Formula:

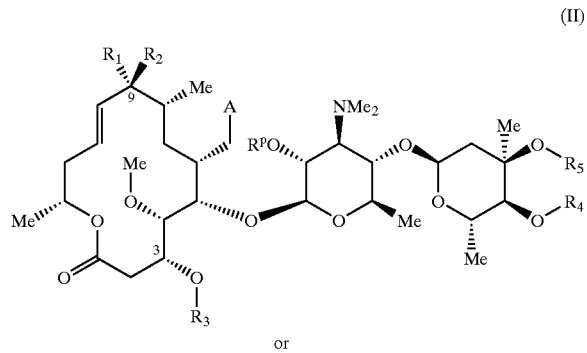

(II)

or

-continued

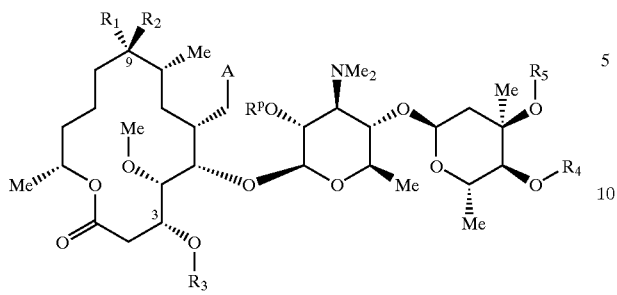

(III)

or a pharmaceutically acceptable salt, ester and prodrug thereof, wherein

A is:
(1) CHO;
(2) $CH_2$-X, where X is selected from the group consisting of
   a. hydroxy or protected hydroxy,
   b. halogen,
   c. NR7R8 wherein R7 and R8 are each independently selected from the group consisting of hydrogen and C1–C6-alkyl optionally substituted with aryl, or heterocyclic groups; or R7 and R8 taken together with the nitrogen atom to which they are connected form a 3- to 7-membered ring which, may optionally contain a hetero function selected from the group consisting of —O—, —NH—, —N(C1–C6-alkyl)-, —N(aryl)-, —N(heteroaryl)- , —S—, —S(O)— and —S(O)2-,
   d. NR7C(O)—R9, where R7 is as previously defined and R9 is selected from the group consisting of
      i. C1–C6-alkyl optionally substituted with aryl, substituted aryl, heterocyclic or substituted heterocyclic,
      ii. aryl,
      iii. substituted aryl,
      iv. heterocyclic, and
      v. substituted heterocyclic,
   e. $S(O)_n$-(C1–C6-alkyl) optionally substituted with aryl or a heterocyclic group where n=0, 1 or 2,
   f. $S(O)_n$-(aryl or heterocyclic group) where n=0, 1 or 2, and
   g. O-(aryl or heterocyclic group);
(3) an aldehyde protecting group
(4) substituted or unsubstituted imidazole, arylimidazole or heteroarylimidazole
(5) substituted or unsubstituted oxazole, aryloxazole or heteroaryloxazole
(6) substituted or unsubstituted thioxazole, arylthioxazole or heteroarylthioxazole
(7) substituted or unsubstituted imidazoline, arylimidazoline or heteroarylimidazoline
(8) substituted or unsubstituted oxazoline, aryloxazoline or heteroaryloxazoline or
(9) substituted or unsubstituted thioxazoline, arylthioxazoline or heteroarylthioxazoline R1 and R2 are each independently selected from the group consisting of
(1) hydrogen,
(2) hydroxy,
(3) protected hydroxy,
(4) OC(O)—C1–C12 alkyl, optionally, substituted with aryl, substituted aryl, heterocyclic, substituted heterocyclic, (5) O—R7 where R7 is as previously defined,
(6) halogen, and
(7) R1 and R2 taken together are oxo;

R3, R4 and R5 are each independently selected from the group consisting of
(1) hydrogen,
(2) a hydroxy protecting group, and
(3) C(O)—C1–C12 alkyl, optionally, substituted with aryl, substituted aryl, heterocyclic, substituted heterocyclic. O—R7 or NR7R8 where R7 and NR7R8 are as previously defined; and $R^P$) is hydrogen or a hydroxy protecting group.

2. A compound according to claim 1 which is represented by Formula II.

3. A compound according to claim 1 which is represented by Formula III.

4. A compound according to claim 1 which is selected from the group consisting of:

Compound of Formula II wherein A=CHO, R1=OH, R2=H, R3=Ac, R4=C(O)CH2CHMe2, R5=H, $R^P$=H;
Compound of Formula II wherein A=CHO, R1=OH, R2=H, R3=H, R4=C(O)CH2CHMe2, R5=H, $R^P$=H;
Compound of Formula II wherein A=CHO, R1=OH, R2=H, R3=H, R4=C(O)CH2CH2CH3, R5=H, $R^P$=H;
Compound of Formula II wherein A=CHO, R1=OH, R2=H, R3=H, R4=C(O)CH2CH3, R5=H, $R^P$=H;
Compound of Formula II wherein A=CHO, R1=OH, R2=H, R3=H, R4=C(O)CH3, R5=H, $R^P$=H;
Compound of Formula II wherein A=CHO, R1=OH, R2=H, R3=H, R4=H, R5=H, $R^P$=H;
Compound of Formula II wherein A=CHO, R1=OH, R2=H, R3=C(O)CH3, R4=C(O)CH2CH2CH3, R5=H, $R^P$=H;
Compound of Formula II wherein A=CHO, R1=OH, R2=H, R3=C(O)CH3, R4=C(O)CH2CH3, R5=H, $R^P$=H;
Compound of Formula II wherein A=CHO, R1=OH, R2=H, R3=C(O)CH3, R4=C(O)CH3, R5=H, $R^P$=H;
Compound of Formula II wherein A=CHO, R1=OH, R2=H, R3=C(O)CH3, R4=H, R5=H, $R^P$=H;
Compound of Formula II wherein A=CHO, R1=OAc, R2=H, R3=C(O)CH2CH3 R4=C(O)CH2CH2CH3, R5=Ac, $R^P$=H;
Compound of Formula II wherein A=CHO, R1=OH, R2=H, R3=H, R4=C(O)CH2CH3, R5=C(O)CH2CH3, $R^P$=H:
Compound of Formula II wherein A=CH2Br, R1=OH, R2=H, R3=Ac, R4=C(O)CH2CHMe2, R5=H, $R^P$=H;
Compound of Formula II wherein A=CH2F, R1=OH, R2=H, R3=Ac, R4=C(O)CH2CHMe2, R5=H, $R^P$=H;
Compound of Formula II wherein A=CH2NMe(Bn), R1=OH, R2=H, R3=Ac, R4=C(O)CH2CHMe2, R5=H, $R^P$=H;
Compound of Formula II wherein A=CH(OMe)2, R1=OH, R2=H, R3=Ac, R4=C(O)CH2CHMe2, R5=H, $R^P$=H;
Compound of Formula II wherein A=CH2OH, R1=OBn, R2=H, R3=Ac, R4=C(O)CH2CHMe2, R5=H, $R^P$=H;
Compound of Formula II wherein A=CHNOPh, R1=OH, R2=H, R3=Ac, R4=C(O)CH2CHMe2, R5=H, $R^P$=H;
Compound of Formula II wherein A=CHNOCH2CH3, R1=OH, R2=H, R3=Ac R4=C(O)CH2CHMe2, R5=H, $R^P$=H;
Compound of Formula II wherein A=CHNOCH3, R1=OH, R2=H, R3=Ac, R4=C(O)CH2CHMe2, R5=H, $R^P$=H;
Compound of Formula II wherein A=CHNOH, R1=OH, R2=H, R3=Ac, R4=C(O)CH2CHMe2, R5=H, R=H;
Compound of Formula II wherein A=CH2OH, R1=OH, R2=H, R3=Ac, R4=C(O)CH2CHMe2, R5=H, $R^P$=H;
Compound of Formula III wherein A=CHO, R1=OH, R2=H, R3=Ac R4=C(O)CH2CHMe2, R5=H, $R^P$=H;

Compound of Formula III wherein R1=CH2OH, R1=OH, R2=H, R3=Ac R4=C(O)CH2CHMe2, R5=H, $R^P$=H;

Compound of Formula II wherein A=CHO, R1=OAc, R2=H, R3=Ac, R4=C(O)CH2CHMe2, R5=H, $R^P$=H;

Compound of Formula II wherein A=CHO, R1=OC(O)CH2CH2C(O)OH, R2=H, R3=Ac, R4=C(O)CH2CHMe2, R5=H, $R^P$=H;

Compound of Formula II wherein A=CHO, R1=OC(O)Ph, R2=H, R3=Ac, R4=C(O)CH2CHMe2, R5=H, $R^P$=H;

Compound of Formula II wherein A=CH2[(4-methyl)-1-piperazinyl], R1=OH, R2=H, R3=Ac, R4=C(O)CH2CHMe2, R5=H, $R^P$=H;

Compound of Formula II wherein A=CH2[(4- phenyl)-1-piperazinyl], R1=OH, R2=H, R3=Ac, R4=C(O)CH2CHMe2, R5=H, $R^P$=H;

Compound of Formula II wherein A=CH2NMe2, R1=OH1, R2=H, R3=Ac, R4=C(O)CH2CHMe2, R5=H, $R^P$=H;

Compound of Formula II wherein A=CHO, R1 and R2=O, R3=Ac, R4=C(O)CH2CHMe2, R5=H, $R^P$=H;

Compound of Formula II wherein A CHNNH2, R1=OH, R2=H, R3=Ac, R4=C(O)CH2CHMe2, R5=H, $R^P$=H;

Compound of Formula II wherein A=CHNNMe2, R1=OH, R2=H, R3=Ac R4=C(O)CH2CHMe2, R5=H, R1H;

Compound of Formula II wherein A=CH=N-(N-morpholine), R1=OH, R2=H, R3=Ac, R4=C(O)CH2CHMe2, R5=H, $R^P$=H;

Compound of Formula II wherein A=CH(OMe)2, R1=H, R2=OH, R3=Ac R4=C(O)CH2CHMe2, R5=H, $R^P$=H;

Compound of Formula III wherein A=CH(OMe)2, R1=H, R2=OH, R3=Ac R4=C(O)CH2CHMe2, R5=H, $R^P$=H;

Compound of Formula II wherein A=CH(OMe)2, R1=Cl, R2=H, R3=Ac R4=C(O)CH2CHMe2, R5=H, $R^P$=H;

Compound of Formula II wherein A=CHO, R1=H, R2=OH, R3=Ac R4=C(O)CH2CHMe2, R5=H, $R^P$=H;

Compound of Formula III wherein A=CH(OMe)2, R1=H, R2=OH, R3=Ac R4=C(O)CH2CHMe2, R5=H, $R^P$=H;

Compound of Formula III wherein A=CHO, R1=H, R2=OH, R3=Ac R4=C(O)CH2CHMe2, R5=H, $R^P$=H;

Compound of Formula II wherein A=CH(OMe)2, R1=OAc, R2=H, R3=Ac R4=C(O)CH2CHMe2, R5=H, $R^P$=H; and Compound of Formula III wherein A=CHO, R1 and R2=O, R3=Ac, R4=C(O)CH2CHMe2, R5=H, $R^P$=H.

5. A compound according to claim 2 wherein A=CHO, R1=OH, R2=H, R3=Ac, R4=C(O)CH2CHMe2, R5=H and $R^P$=H.

6. A compound according to claim 2 wherein A=CHO, R1=H, R2=OH, R3=Ac, R4=C(O)CH2CHMe2, R5=H and $R^P$=H.

7. A compound according to claim 2 wherein A=CHO, R1=OH, R2=H, R3=H, R4=C(O)CH2CH2CH3, R5=H, $R^P$=H.

8. A pharmaceutical composition for treating bacterial infections comprising a therapeutically effective amount of a compound of claim 1, or a pharmaceutically acceptable salt, ester or prodrug thereof in combination with a pharmaceutically acceptable carrier.

9. A method for treating bacterial infections comprising administering to a mammal in need of such treatment a pharmaceutical composition containing a pharmaceutically effective amount of a compound of claim 1 or a pharmaceutically acceptable salt, ester or prodrug thereof.

10. A process for preparing a compound represented by Formula II as defined in claim 1 comprising:

(a) reacting a compound represented by the Formula

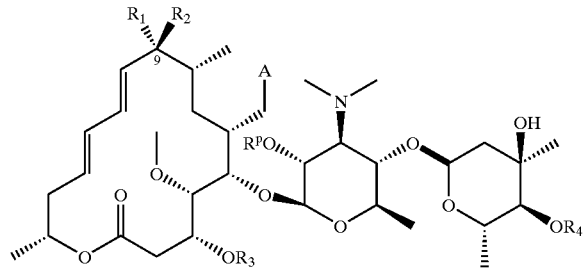

wherein A, R1, R2, R3, R4, and $R^P$ are as defined in claim 1 with a ruthenium or molybdenum catalyst, optionally in the presence of an additive selected from the group consisting of ethylene, 1-hexene, isobutylene, titanium (IV) isopropoxide and aluminum (III) propoxide in an organic solvent to provide a compound of Formula II.

11. A process for the preparation of a compound represented by Formula III as defined in claim 1 comprising hydrogenating a compound represented by Formula II as defined in claim 1 with a palladium catalyst in the presence of hydrogen in an organic solvent to provide a compound of Formula III.

* * * * *